United States Patent [19]

Kesselman et al.

[11] Patent Number: 4,740,373
[45] Date of Patent: Apr. 26, 1988

[54] STABILIZATION OF MULTIVITAMIN/TRACE ELEMENTS FORMULATIONS

[75] Inventors: Morris Kesselman, Belmar, N.J.; Abdur R. Purkaystha, Bronx; James Cahill, Riverdale, both of N.Y.

[73] Assignee: USV Pharmaceutical Corporation

[21] Appl. No.: 866,842

[22] Filed: May 27, 1986

[51] Int. Cl.$^4$ ............... A61K 33/34; A61K 31/07; A61K 31/195; A61K 31/44
[52] U.S. Cl. ....................... 424/141; 514/52; 514/167; 514/168; 514/249; 514/251; 514/276; 514/458; 514/474; 514/499; 514/548; 514/681; 514/905; 514/970
[58] Field of Search ............... 514/167, 168, 970, 52, 514/905, 251, 276, 458, 548, 681, 249, 474, 499; 424/141

[56] References Cited

U.S. PATENT DOCUMENTS

| | | | |
|---|---|---|---|
| 2,731,390 | 1/1956 | Tansey et al. | 424/308 |
| 3,899,598 | 8/1975 | Fischer et al. | 426/73 |
| 3,914,419 | 10/1975 | Haeger et al. | 424/237 |
| 3,932,634 | 1/1976 | Kardys | 424/237 |
| 4,228,159 | 10/1980 | MacMillan | 424/145 |
| 4,268,529 | 5/1981 | Davis et al. | 426/72 |

FOREIGN PATENT DOCUMENTS

| | | | |
|---|---|---|---|
| 0161915 | 11/1985 | European Pat. Off. | 514/970 |
| 58-198416 | 11/1983 | Japan | 514/970 |
| 1080626 | 8/1967 | United Kingdom . | |

OTHER PUBLICATIONS

Chem. Abst., 99:10856s (1983)–Heidt.
Chem. Abst., 105:11967h (1986)–Vervloet et al.
The Effects of Ascorbic Acid and Trace Elements on Vitamin $B_{12}$ Assays, J. Am. Pharm. Assoc., 43:87–90, 1954.

Primary Examiner—Douglas W. Robinson

[57] ABSTRACT

Disclosed are aqueous multivitamin/trace elements formulations stabilized by a water soluble, organic acid that contains carbon-to-carbon unsaturation and water soluble salts thereof selected from the group consisting of maleic acid, fumaric acid, maleamic acid and acrylic acid.

6 Claims, No Drawings

STABILIZATION OF MULTIVITAMIN/TRACE ELEMENTS FORMULATIONS

BACKGROUND OF THE INVENTION

1. Field of the Invention

This invention relates to a method of stabilizing aqueous parenteral solutions of multivitamins in the presence of trace elements and compositions produced thereby for human and veterinary administration.

As is well known, in addition to the various basic nutritive materials which are required by humans and animals, a variety of other nutrients and essential elements are also required for the maintenance of good health. The present invention is directed to nutrients and essential elements, sometimes called "micronutrients", from which relatively very small amounts are needed to provide a well-balanced, healthy diet. For convenience, the compositions of the invention will be described as relate to humans, however, the same can as well be used for veterinary purposes. While the compositions of the invention may be used as regular supplements to nutrients obtained through the digestive system, it especially concerns total parenteral nutrition to provide nutritional support for persons unable to meet their nutritional requirements through the digestive system, i.e. for nutritional rehabilitation of patients.

Total parenteral nutrition (TPN) has been used for many years and an expanded knowledge of nutritional requirements led to the development of a wide array of products from which the TPN solutions can be formulated. The Nutritional Advisory Group of the American Medical Association (AMA) has developed recommendations for the parenteral use of multivitamin preparations. The guidelines for adult formulations are as follows (JPEN 3: 258–262, 1979)

| Vitamin | Daily Administration |
| --- | --- |
| A | 3,300 IU |
| D | 200 IU |
| E | 10 IU |
| Ascorbic Acid | 100 mg |
| Folacin | 400 mcg |
| Niacin | 40 mg |
| Riboflavin | 3.6 mg |
| Thiamin | 3 mg |
| Pyridoxine (B6) | 4 mg |
| Cyanocobalamin (B12) | 5 mcg |
| Pantothenic Acid | 15 mg |
| Biotin | 60 mcg |

The medical profession has focused increasing attention on the importance of trace elements in the nutritional management of medical, surgical, and traumatic conditions. The AMA has also published guidelines for trace element preparations for parenteral use (JPEN 3: 263–267, 1979):

| Trace Elements | Daily Administration |
| --- | --- |
| Zinc | 2.5–4 mg |
| Copper | 0.5–1.5 mg |
| Chromium | 10–15 mcg |
| Manganese | 0.15–0.8 mg |

The AMA did not address other trace elements, however, there are increasing data for the role of these various trace elements in good nutritional support. It is generally known that the "essential elements", i.e. calcium, magnesium, sodium and potassium, furthermore zinc, manganese, copper, cobalt, chromium, iron, molybdenum, vanadium, selenium and nickel are indispensable for the normal function of living organisms. The essential elements are the constituents or activators of numerous enzyme systems, they are in close correlation with the level of certain vitamins in the organism and with the function of the hormone system. The deficiency of essential elements greatly suppresses the biosynthesis of proteins, enzymes, hormones and other biologically active substances required to control the normal functions of the living organism as a whole.

The JPEN 5: 424–429, 1981 reports on health disorders associated with the insufficiency of some essential trace elements in TPN: Zinc deficiency manifests in a variety of diseases including acrodermatitic skin lesions, impaired immunity, poor growth, impaired wound healing, and mental disturbances; copper deficiency results in hematologic abnormalities, usually anemia with leukopenia and neutropenia; chromium deficiency has been recognized to play a role in glucose intolerance, weight loss, peripheral neuropathy or encephalopathy; and selenium deficiency in experimental animals was observed to cause liver necrosis, pancreatic atrophy, and muscular dystrophy. Manganese is an actuator of several enzymes being involved in protein synthesis and function of the central nervous system. It is essential for bone structure and reproduction.

2. Description of the Prior Art

In general, liquid multivitamin preparations of the prior art are packaged in two separate vials or syringes, or double compartment vials or syringes to prevent interaction between some of the vitamins. Such interaction results in discoloration of the solution and loss of potency. Another approach to solve the interaction problem resulted in lyophilizing multivitamin preparations and reconstituting the same just prior to injection.

The ingredients interaction problem is even more serious when, in addition to containing multivitamins, the preparation also contains trace elements, especially copper. To circumvent the problem, the prior art, again, provided a two or three package system, one or two of which contained the multivitamins and one the trace elements. The contents of the packages were either separately infused into the patient or were admixed just prior to infusion. While the former method is undesirably cumbersome, the latter method is unsatisfactory for the reason that the reactions between the trace elements and the multivitamins are so rapid that the browning reaction and turbidity can be observed within minutes of admixing the two phases. In addition, the interaction could cause clogging of the infusion needle and the introduction of solid particles into the vein of the patient. This problem could be especially serious with infusions mixed several hours prior to addition to TPN solutions.

The present invention is designed to solve the above-described problems and to provide multivitamin/trace elements formulations in aqueous solution for parenteral administration to patients.

SUMMARY OF THE INVENTION

It is a main object of the present invention to administer to patients multivitamins and trace elements together as one entity in an infusion mixture. Heretofore such administration was not possible due to the instantaneous reaction of trace elements with several of the vitamins forming darkly colored, turbid solutions with heavy precipitation occuring within minutes. Examples of such undesirable reactions include reaction of copper with vitamin C, riboflavin, folic acid and vitamin $B_{12}$.

It is another object of the present invention to provide a multivitamin/trace elements formulation which is stable for at least 4 to 8 hours at room temperature or 12 to 24 hours refrigerated so as to allow normal manipulative time in hospital infusion.

It has been surprisingly discovered that the rapid inter-reactions between vitamins and trace elements can be prevented by the use of a water soluble, organic acid that contains carbon-to-carbon unsaturation and water soluble salts thereof. Such organic acids include: maleic acid, fumaric acid, maleamic acid and acrylic acid. Water soluble saturated weak organic acids, such as citric acid, acetic acid, tartaric acid, gluconic acid, succinic acid, lactic acid, and oxalic acid showed no stabilizing effects. Cyanoacetic acid which has an unsaturated carbon to nitrogen bond was also ineffective in stabilizing the multivitamin/trace elements formulations.

In accordance with this discovery, several embodiments of the invention are provided as will be described hereunder.

a. One embodiment of the present invention lies in an injectable, two compartment, one unit vial or syringe, aqueous liquid-liquid preparation of multivitamins/trace elements maintained separately, one of the two compartments, in addition to containing the active ingredients, contains a sufficient amount of a water soluble organic acid having carbon-to-carbon unsaturation to stabilize the injectable combination preparation.

b. Still another embodiment of the present invention is the same as that described in (a) except the container is a two-unit vial or syringe package.

c. A further embodiment of the present invention provides for lyophilization of the respective solution or solutions referred to in (a) and (b) which are reconstituted prior to infusion.

The stabilizer can be added separately or combined with either multivitamins or trace elements.

The various embodiments of the present invention are useful for adult, pediatric, neonatal or TPN regimen and also for veterinary application.

It has been found that a molar ratio of 3 to 30 times of stabilizer to combined trace elements is necessary to effectively stabilize either the multivitamin or the trace elements containing solution which corresponds to about 0.5 to 5.0% w/v of stabilizer in the solution. The preferred method of stabilization is the use of 5 to 10 molar ratio of the water soluble unsaturated organic acid in the trace elements solution. While the mechanism of stabilization is not understood, it is postulated that stabilization is due to weak bonding of the trace element(s) to the unsaturated carbon-carbon (double) bond.

DETAILED DESCRIPTION OF THE INVENTION

In general, the multivitamin/trace elements formulations of the present invention are directed by therapeutic considerations based on judgements of those skilled in the art of nutrition. For special deficiencies additional components or amounts may be added. Tables I and II show the amounts of the various vitamins and trace elements considered advantageous for use in TPN formulations.

TABLE I

| Vitamin Range | | | |
|---|---|---|---|
| Active | Forms | Broad Range | Preferred Range* |
| Vitamin A, IU | alcohol, palmitate, acetate | 230–10,000 | 3,300–5,000 |
| Vitamin $B_1$, mg | hydrochloride, mononitrate, phosphate esters | 0.05–45.0 | 3.0–6.0 |
| Vitamin $B_2$, mg | riboflavin, riboflavin-5-phosphate sodium salt | 0.07–10.0 | 3.0–6.0 |
| Vitamin $B_6$, mg | hydrochloride | 0.04–12.0 | 4.0–6.0 |
| Vitamin C, mg | Vitamin C, sodium ascorbate | 4–1,000 | 100–200 |
| Vitamin D, IU | ergocalciferol, calciferol | 44–1,000 | 200–400 |
| Vitamin E, IU | d or dl tocopheryl, d or dl tocopheryl acetate | 0.66–10 | 5–10 |
| Niacinamide, mg | niacinamide, niacin | 0.25–100 | 40–60 |
| Pantothenic Acid, mg | d-panthenol, calcium pantothenate | 0.3–25 | 10–15 |
| Vitamin K, mg | phytonadione, menadiole, menadione bisulfite, menadiol phosphate | 0.04–1.0 | 0.10–0.5 |
| Biotin, mcg | biotin | 10–100 | 25–60 |
| Folic Acid, mcg | folic acid, sodium folate | 5–800 | 400–600 |
| Vitamin $B_{12}$, mcg | cyanocobalamin, cobalamin, hydroxy cobalamin | 0.04–10 | 2–5 |

*Preferred Range for adult formula

TABLE II

| Trace Element Range | | | |
|---|---|---|---|
| Active | Forms | Broad Range | Preferred Range* |
| Zinc | chloride, sulfate, acetate, citrate, lactate, nitrate, tartrate | 100 mcg–10 mg | 3–6 mg |
| Copper | chloride, sulfate, acetate, nitrate, gluconate | 20 mcg–2.8 mg | 0.4–1.5 mg |
| Manganese | chloride, sulfate acetate, nitrate | 2 mcg–2.5 mg | 0.15–0.80 mg |
| Chromium | chloride, sulfate, acetate, nitrate | 0.14 mcg–20 mcg | 10–15 mcg |

*Preferred Range for adult formula

In addition to the active ingredients of vitamins and trace elements, excipients conventionally used in infusable solutions can be used, illustrative examples and amounts of which are shown in Table III.

TABLE III

| Excipients | |
|---|---|
| Antioxidants and Stabilizers (0.005–2.0% w/v) | thiourea, thioglycerol, thiosorbitol, cysteine, glycine, sodium formaldehyde sulfoxylate, butylated hydroxyanisole, butylated hydroxytoluene, nordihydrogluaiaretic acid, ethyl hydrocaffeate, gentisic acid ethonalamide, propyl gallate, ascorbyl palmitate, iron salts. |
| Solvents (0.01 to 30% w/v) | propylene glycol, glycerin, alcohol, polyethylene glycol. |
| Solubilizers (0.01 to 5% w/v) | polyoxylated sorbitol fatty acid esters, polyoxylated vegetable oils. |
| Preservatives | (for multidose units) parabens, chlorbutanol, |

TABLE III-continued

| Excipients | |
|---|---|
| (0.01 to 1.0% w/v) | phenol, benzyl alcohol. |

The multivitamin/trace elements formulations of the present invention may be prepared using commercially available ingredients by methods well-known in the prior art. (Suppliers of raw materials include Hoffman-LaRoche Co., R. W. Greef & Co., H. Reisman Corp., Roussel Corp. and Rhone Poulenc Inc.)

The following examples will illustrate formulations according to the present invention.

EXAMPLE 1 (Adult)

Ten grams of maleic acid is dissolved in 900 mL of water for injection. To this is added
- 0.536 g: copper chloride ($2H_2O$),
- 1.68 g: zinc chloride,
- 0.364 g: manganese chloride ($4H_2O$)
- 10.25 mg: chromium chloride ($6H_2O$).

The mixture is stirred until the solution is dissolved and adjusted to 1 liter volume.

Five mL of this mixture containing
- 1.0 mg: copper
- 4.0 mg: zinc
- 0.5 mg: manganese
- 10 mcg: chromium is added to a vial of lyophilized or liquid multivitamin solution containing the following vitamins per unit dose:
- 3,300 IU: vitamin A
- 200 IU: vitamin D
- 10 IU: vitamin E
- 0.15 mg: vitamin $K_1$
- 6.0 mg: thiamin
- 3.6 mg: riboflavin
- 6.0 mg: pyridoxine
- 40 mg: niacinamide
- 60 mcg: biotin
- 5.0 mcg: vitamin $B_{12}$
- 15.0 mg: pantothenic acid
- 600 mcg: folic acid
- 200 mg: ascorbic acid.

EXAMPLE 2 (Adult)

Five grams of fumaric acid is dissolved in 900 mL of water for injection and
- 1.18 g: copper sulfate ($5H_2O$),
- 3.54 g: zinc sulfate ($7H_2O$),
- 0.307 g: manganese sulfate ($H_2O$); and
- 15.04 mg: chromium sulfate are added and dissolved.

The solution is then brought to 1 liter volume. A 5 mL aliquot is taken containing
- 1.5 mg: copper
- 4 mg: zinc
- 0.5 mg: manganese
- 10 mcg: chromium and is added to a liquid or lyophilized multivitamin mixture for infusion purposes, the multivitamin mixture containing the following vitamins:
- 3,300 IU: vitamin A
- 200 IU: vitamin D
- 10 IU: vitamin E
- 3.0 mg: thiamin
- 3.6 mg: riboflavin
- 4.0 mg: pyridoxine
- 40 mg: niacinamide
- 60 mcg: biotin
- 5.0 mcg: vitamin $B_{12}$
- 15.0 mg: pantothenic acid
- 400 mcg: folic acid
- 100 mg: ascorbic acid.

EXAMPLE 3 (Adult)

Twenty grams of tris maleate is added to 900 mL of water for injection and stirred to dissolve. Then the following trace elements are added and dissolved:
- 0.79 g: copper sulfate ($5H_2O$),
- 2.1 g: zinc chloride,
- 0.144 g: manganese chloride ($4H_2O$), and
- 10.25 mg: chromium chloride ($6H_2O$).

The solution is q.s. to 1.0 liter and 5 mL aliquot containing
- 1.0 mg: copper
- 5 mg: zinc
- 0.2 mg: manganese
- 10 mcg: chromium is mixed with one unit dose of multivitamin solution for infusion delivery. The vitamin concentration is shown in Example 1.

EXAMPLE 4 (Adult)

Twenty five grams of maleic acid is dissolved in 900 mL water and
- 1.072 g: copper chloride ($2H_2O$),
- 2.52 g: zinc chloride,
- 0.144 g: manganese chloride ($4H_2O$),
- 10.25 mg: chromium chloride ($6H_2O$)

are added and dissolved. The solution is q.s. to 1.0 liter. Five mL aliquot containing
- 2 mg: copper
- 6 mg: zinc
- 0.2 mg: manganese
- 10 mcg: chromium is added to a unit vial of multivitamin of lyophilized multivitamin solution. This is mixed for subsequent addition to the infusion solution. The concentration of vitamins is the same as that shown in Example 1.

EXAMPLE 5 (Adult)

Twenty grams of sodium maleate is dissolved in 900 mL water for injection. To this is added
- 0.5366 g: copper chloride ($2H_2O$),
- 1.68 g: zinc chloride,
- 0.364 g: manganese chloride ($4H_2O$),
- 10.25 mcg: chromium chloride ($6H_2O$).

This mixture is stirred until solution is complete and adjusted to 1 liter. Five mL of this mixture, containing the same concentration of trace elements as Example 1, is added to a unit vial of lyophilized or liquid multivitamins.

The composition of the multivitamin mixture used in this example is
- 3,300 IU: vitamin A
- 200 IU: vitamin D
- 10 IU: vitamin E
- 3.0 mg: thiamin
- 3.6 mg: riboflavin
- 4.0 mg: pyridoxine
- 40 mg: niacinamide
- 60 mcg: biotin
- 5.0 mcg: vitamin $B_{12}$
- 15.0 mg: pantothenic acid 400 mcg: folic acid
100 mg: ascorbic acid
2.5 mg: thiourea.

EXAMPLE 6 (Pediatric)

Five grams of maleic acid is dissolved in 900 mL water for injection and
  0.161 g: copper chloride (2H$_2$O),
  0.63 g: zinc chloride,
  0.072 g: manganese chloride (4H$_2$O), and
  2.05 mg: chromium chloride (6H$_2$O)
are added and dissolved. The solution is brought to 1 liter.
Five mL of this mixture containing
  0.3 mg: copper
  1.5 mg: zinc
  0.1 mg: manganese
  2 mcg: chromium
is added to a unit vial of lyophilized or liquid pediatric multivitamin solution. The composition of multivitamin pediatric solution is
  2,300 IU: vitamin A
  400 IU: vitamin D
  7 IU: vitamin E
  0.2 mg: vitamin K$_1$
  17 mg: niacinamide
  1.4 mg: riboflavin
  1.2 mg: thiamin
  1.0 mg: pyridoxine
  5.0 mg: pantothenic acid
  80 mg: ascorbic acid
  20 mcg: biotin
  1.0 mcg: vitamin B$_{12}$
  140.0 mcg: folic acid.

EXAMPLE 7 (NEONATAL)

2.5 grams of maleic acid is dissolved in 900 mL water for injection and
  0.032 g: copper chloride (4H$_2$O),
  0.25 g: zinc chloride,
  0.014 g: manganese chloride (4H$_2$O), and
  0.61 mg: chromium chloride (6H$_2$O)
are added and dissolved. The solution is q.s. to 1 liter and 5 mL of this mixture containing
  0.06 mg: copper
  0.6 mg: zinc
  0.02 mg: manganese
  0.6 mcg: chromium
is added to a unit vial of lyophilized or liquid multivitamin containing the following vitamins:
  1,400 IU: vitamin A
  200 IU: vitamin D
  4 IU: vitamin E
  0.1 mg: vitamin K$_1$
  10 mg: niacinamide
  0.8 mg: riboflavin
  0.7 mg: thiamin
  0.6 mg: pyridoxine
  3.0 mg: pantothenic acid
  50 mg: vitamin C
  12 mcg: biotin
  0.6 mcg: vitamin B$_{12}$
  90.0 mcg: folic acid.

EXAMPLE 8 (Adult)

0.536 g: copper chloride (2H$_2$O),
  1.26 g: zinc chloride,
  0.144 g: manganese chloride (4H$_2$O),
  10.25 mg: chromium chloride (6H$_2$O)
are dissolved in 900 mL water for injection. The solution is adjusted to pH 2 with hydrochloric acid and the volume is brought to 1 liter.
5 mL of this mixture containing
  1.0 mg: copper
  3.0 mg: zinc
  0.2 mg: manganese
  10 mcg: chromium
is added to a unit vial of lyophilized or liquid multivitamins containing the following vitamins:
  3,300 IU: vitamin A
  200 IU: vitamin D
  10 IU: vitamin E
  0.15 mg: vitamin K$_1$
  6.0 mg: thiamin
  3.6 mg: riboflavin
  6.0 mg: pyridoxine
  40 mg: niacinamide
  60 mcg: biotin
  5.0 mcg: vitamin B$_{12}$
  15.0 mg: pantothenic acid
  600 mcg: folic acid
  200 mg: ascorbic acid
  1% w/v: maleic acid
  0.3 mg: iron peptonate
  1.0 mg: disodium edetate Physical stability data of a multivitamin formulation containing the vitamins of Table I in the presence of trace elements of Table II are shown in Table IV. In one set of experiments no stabilizer was used; in another set of experiments the water soluble saturated, weak organic acid stabilizers (citric, acetic, tartaric, gluconic, succinic, lactic, oxalic acids) were used; while in the third set of experiments, maleic acid was used as the stabilizer.

TABLE IV

| | Physical Stability | | |
|---|---|---|---|
| Time | No Stabilizer | Saturated Weak Organic Acids | Maleic Acid Stabilizer |
| Initial (15 seconds) | Turbid Severe darkening | Turbid Severe darkening | Clear Very slight color change |
| 2 Hours Room temp. | Slight precipitation Severe darkening | Slight precipitation Severe darkening | Clear, no precipitate No further color change |
| 4 Hours Room temp. | Moderate precipitation Severe darkening | Moderate precipitation Severe darkening | Clear, no precipitate No further color change |
| 8 Hours Room temp. | Heavy reddish brown precipitate Severe darkening | Heavy reddish brown precipitate Severe darkening | Clear, no precipitate No further color change |
| 24 Hours | Heavy reddish brown | Heavy reddish brown | Clear, no precipitate |

TABLE IV-continued

| | Physical Stability | | |
|---|---|---|---|
| Time | No Stabilizer | Saturated Weak Organic Acids | Maleic Acid Stabilizer |
| Room temp. | precipitate<br>Severe darkening | precipitate<br>Severe darkening | Slight color change from original |
| 24 Hours Refrigerated | Heavy reddish brown precipitate<br>Severe darkening | Heavy reddish brown precipitate<br>Severe darkening | Clear, no precipitate<br>No color change from original |

Table V shows results of chemical stability tests conducted on vitamin C, vitamin $B_1$, folic acid, and vitamin $B_{12}$ contained in a multivitamin formulation according to Table I in the presence of the trace elements of Table II. In one set of experiments the unsaturated water soluble acid stabilizer was used, while in another set of experiments the stabilizer was omitted. The remainder of the vitamins of Table I, namely, niacinamide, vitamin $B_6$, vitamin $B_2$, biotin, vitamin K, pantothenic acid, and vitamins A, D and E were found to be relatively stable in the presence of the trace elements without the presence of stabilizers.

TABLE V

| | Chemical Stability | |
|---|---|---|
| | No Stabilizer | Stabilizer |
| | Vitamin C<br>% Loss | |
| 2 Hrs. RT | 14 | 4 |
| 4 Hrs. RT | 23 | 5 |
| 6 Hrs. RT | 30 | 5 |
| 8 Hrs. RT | 40 | 5 |
| 24 Hrs. RT | 93 | 12 |
| 24 Hrs. Refrig | 61 | 5 |
| | Vitamin $B_1$<br>% Loss | |
| 2 Hrs. RT | 6 | 0 |
| 4 Hrs. RT | 14 | 2 |
| 6 Hrs. RT | 8 | 7 |
| 8 Hrs. RT | 15 | 4 |
| 24 Hrs. RT | 16 | 3 |
| 24 Hrs. Refrig | 11 | 1 |
| | Folic Acid<br>% Loss | |
| 2 Hrs. RT | 9 | 3 |
| 4 Hrs. RT | 10 | 3 |
| 6 Hrs. RT | — | 2 |
| 8 Hrs. RT | — | 5 |
| 24 Hrs. RT | 43 | 2 |
| 24 Hrs. Refrig | 38 | 0 |
| | Vitamin $B_{12}$<br>% Loss | |
| 2 Hrs. RT | — | — |
| 4 Hrs. RT | 66 | 1 |
| 6 Hrs. RT | — | — |
| 8 Hrs. RT | 100 | 0 |
| 24 Hrs. RT | 100 | 7 |
| 24 Hrs. Refrig | — | — |

The preceeding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A stable aqueous multivitamin/trace elements preparation for parenteral administration comprising per milliliter of aqueous solution at least two vitamins selected from the group consisting of:
   230–10,000 IU: Vitamin A,
   0.05–45.0 mg: Vitamin $B_1$,
   0.07–10.0 mg: Vitamin $B_2$,
   0.04–12.0 mg: Vitamin $B_6$,
   4–1,000 mg: Vitamin C,
   44–1,000 IU: Vitamin D,
   0.66–10 IU: Vitamin E,
   0.25–100 mg: Niacinamide,
   0.3–25 mg: Pantothenic Acid,
   0.04–1.0 mg: Vitamin K,
   10–100 mcg: Biotin,
   5–800 mcg: Folic Acid,
   0.04–10 mcg: Vitamin $B_{12}$;
   20 mcg–2.8 mg of the trace element Copper;
at least one trace element selected from the group consisting of:
   100 mcg–10 mg: Zinc
   2 mcg–2.5 mg: Manganese
   0.14 mcg–20 mcg: Chromium;
and about 0.5 to 5.0% w/v of a stabilizer selected from the group consisting of:
   maleic acid,
   fumaric acid,
   maleamic acid,
   and a water soluble salt thereof.

2. A stable aqueous multivitamin/trace elements preparation for parenteral administration comprising per milliliter of aqueous solution at least two vitamins selected from the group consisting of:
   3,300–5,000 IU: Vitamin A,
   3.0–6.0 mg: Vitamin $B_1$,
   3.0–6.0 mg: Vitamin $B_2$,
   4.0–6.0 mg: Vitamin $B_6$,
   100–200 mg: Vitamin C,
   200–400 IU: Vitamin D,
   5–10 IU: Vitamin E,
   40–60 mg: Niacinamide,
   10–15 mg: Pantothenic Acid,
   0.10–0.5 mg: Vitamin K,
   25–60 mcg: Biotin,
   400–600 mcg: Folic Acid,
   2–5 mcg: Vitamin $B_{12}$;
   0.4–1.5 mg of the trace element Copper;
at least one trace element selected from the group consisting of:
   3–6 mg: Zinc
   0.15–0.80 mg: Manganese
   10–15 mcg: Chromium;
and about 0.5 to 5.0% w/v of a stabilizer selected from the group consisting of:
   maleic acid,
   fumaric acid,
   maleamic acid,
   and a water soluble salt thereof.

3. A stable aqueous multivitamin/trace elements preparation for parenteral administration comprising per milliliter of aqueous solution at least two vitamins selected from the group consisting of:
   0.05–45.0 mg: Vitamin $B_1$,
   0.07–10.0 mg: Vitamin $B_2$, 4-1,000 mg: Vitamin C,
5-800 mcg: Folic Acid,
20 mcg-2.8 mg of the trace element Copper;
at least one trace element selected from the group consisting of:
100 mcg-10 mg: Zinc
2 mcg-2.5 mg: Manganese
0.14 mcg-20 mcg: Chromium;
and about 0.5 to 5.0% w/v of a stabilizer selected from the group consisting of:
maleic acid,
fumaric acid,
maleamic acid,
and a water soluble salt thereof.

4. A stable aqueous multivitamin/trace elements preparation for parenteral administration comprising per milliliter of aqueous solution at least two vitamins selected from the group consisting of:
3.0-6.0 mg: Vitamin $B_1$,
3.0-6.0 mg: Vitamin $B_2$,
100-200 mg: Vitamin C,
400-600 mcg: Folic Acid,
0.4-1.5 mg of the trace element Copper;
at least one trace element selected from the group consisting of:
3-6 mg: Zinc
0.15-0.80 mg: Manganese
10-15 mcg: Chromium;
and about 0.5 to 5.0% w/v of a stabilizer selected from the group consisting of:
maleic acid,
fumaric acid,
maleamic acid,
and a water soluble salt thereof.

5. A stable aqueous multivitamin/trace elements preparation for parenteral administration comprising per milliliter of aqueous solution at least two vitamins selected from the group consisting of:
0.05-45.0 mg: Vitamin $B_1$,
4-1,000 mg: Vitamin C,
5-800 mcg: Folic Acid,
0.04-10 mcg: Vitamin $B_{12}$;
20 mcg-2.8 mg of the trace element Copper;
at least one trace element selected from the group consisting of:
100 mcg-10 mg: Zinc
2 mcg-2.5 mg: Manganese
0.14 mcg-20 mcg: Chromium;
and about 0.5 to 5.0% w/v of a stabilizer selected from the group consisting of:
maleic acid,
fumaric acid,
maleamic acid,
and a water soluble salt thereof.

6. A stable aqueous multivitamin/trace elements preparation for parenteral administration comprising per milliliter of aqueous solution at least two vitamins selected from the group consisting of:
3.0-6.0 mg: Vitamin $B_1$,
100-200 mg: Vitamin C,
400-600 mcg: Folic Acid,
2-5 mcg: Vitamin $B_{12}$;
0.4-1.5 mg of the trace element Copper;
at least one trace element selected from the group consisting of:
3-10 mg: Zinc
0.15-0.80 mg: Manganese
10-15 mcg: Chromium;
and about 0.5 to 5.0% w/v of a stabilizer selected from the group consisting of:
maleic acid,
fumaric acid,
maleamic acid,
and a water soluble salt thereof.

* * * * *